(12) United States Patent
Soto Ramirez et al.

(10) Patent No.: US 11,504,519 B2
(45) Date of Patent: Nov. 22, 2022

(54) RELEASABLE SEAL FOR CATHETER SYSTEM

(71) Applicant: Fresenius Medical Care Holdings, Inc., Waltham, MA (US)

(72) Inventors: Orestes Soto Ramirez, Reynosa (MX); Irving Uziel Hernandez Gomez, Hidalgo, TX (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 217 days.

(21) Appl. No.: 17/009,874

(22) Filed: Sep. 2, 2020

(65) Prior Publication Data

US 2022/0062615 A1 Mar. 3, 2022

(51) Int. Cl.
*A61M 39/10* (2006.01)
*A61M 25/00* (2006.01)
*A61M 1/28* (2006.01)

(52) U.S. Cl.
CPC .... *A61M 39/1055* (2013.01); *A61M 25/0043* (2013.01); *A61M 39/105* (2013.01);
(Continued)

(58) Field of Classification Search
CPC .............. A61M 39/1055; A61M 39/10; A61M 39/105; A61M 39/22; A61M 39/00; A61M 39/06; A61M 39/26; A61M 39/08; A61M 2039/1027; A61M 2039/062; A61M 2039/0626; A61M 2039/0633; A61M 2039/0673; A61M 2039/2433; A61M 2039/244; A61M 2039/0666; A61M 2039/2446; A61M 2039/0009;
(Continued)

(56) References Cited

U.S. PATENT DOCUMENTS

| 4,850,350 A | 7/1989 | Jackson |
| 2003/0187391 A1 | 10/2003 | Hogendijk |

(Continued)

FOREIGN PATENT DOCUMENTS

WO 2022051050 A1 3/2022

OTHER PUBLICATIONS

ISA/EP, "International Search Report and Written Opinion dated Dec. 7, 2021" PCT Application No. PCT/US21/44600, 17 pages.

*Primary Examiner* — Kevin C Sirmons
*Assistant Examiner* — Alexandra Lalonde
(74) *Attorney, Agent, or Firm* — Bass Patent Law, LLC (57) ABSTRACT

The present teachings may generally include a sealing device disposed within a connector (e.g., a patient connector) at an end of catheter tubing, where the sealing device is structurally configured to form a releasable seal for the catheter tubing. That is, when unengaged with a contact portion of another connector or device, the sealing device may be disposed in a first position establishing the seal. Specifically, a channel disposed through a body of the sealing device may be obstructed when in the first position. However, through predetermined engagement with the contact portion of another connector or device, the sealing device may be moved (e.g., rotated) to a second position to establish a fluid pathway through the channel. And, when the predetermined engagement is removed, the sealing device may be structurally configured to automatically move back into the first position to reestablish the seal for the catheter tubing.

20 Claims, 5 Drawing Sheets

(52) U.S. Cl.
CPC ..... *A61M 1/285* (2013.01); *A61M 2025/0018* (2013.01); *A61M 2207/00* (2013.01)

(58) Field of Classification Search
CPC ........ A61M 2039/262; A61M 25/0043; A61M 25/00; A61M 25/0029; A61M 25/003; A61M 25/0074; A61M 25/0075; A61M 25/0097; A61M 2025/0018; A61M 2025/0078; A61M 2205/0216; A61M 2205/0266; A61M 2039/0036; A61M 2039/0214; A61M 39/0208; A61M 5/14593; A61M 31/002; A61M 2005/14513; A61M 5/14276; A61M 5/168
See application file for complete search history.

(56) References Cited

U.S. PATENT DOCUMENTS

| | | |
|---|---|---|
| 2010/0042049 A1 | 2/2010 | Leeflang et al. |
| 2015/0202424 A1* | 7/2015 | Harton .............. A61M 39/1055 604/248 |

* cited by examiner

RELEASABLE SEAL FOR CATHETER SYSTEM

FIELD

The present disclosure generally relates to a releasable seal for a catheter system, e.g., a self-occluding plug within a connector such as a patient connector or the like.

BACKGROUND

Catheters are medical devices that can be inserted into the body of a patient (e.g., a human patient) for various treatments and/or to perform a surgical procedure. Catheters can be inserted into a body cavity, duct, vessel, and the like, for example, to establish drainage, administer fluids such as medicines and the like, establish access by surgical instruments, and so on. Catheters may thus protrude from a patient's body temporarily or permanently, where the end of such a catheter may be structurally configured for connection to other tubing, e.g., a catheter extension. In this manner, the end of a catheter protruding from a patient's body may be referred to as a patient connector, which may be advantageously sealed after a treatment or procedure to prevent leakage therefrom and/or to prevent transmission of unwanted substances therein.

In some existing catheter systems, a patient connector can be structurally configured to receive a pin or the like that can be triggered and inserted by a cooperating connector, where such a pin acts to occlude the patient connector. However, such pins can be dislodged and misplaced, causing a leak or otherwise preventing the sealing of the catheter tubing. Further, the process of inserting such a pin represents another step that a user must take to seal a catheter connection, further complicating what can already be a stressful and/or complicated process. In other existing catheter systems, a clamp or the like can be used to seal tubing of a catheter, but, similar to the pin, such clamps can be misplaced and the use of such clamps requires an extra step in a catheter treatment/procedure. In yet some other existing catheter systems, a cap can be placed on the end of a catheter connector, but such caps have many of the same disadvantages of the aforementioned pins and clamps.

There remains a need for improved techniques for releasably sealing at least a portion of a catheter system.

SUMMARY

The present teachings may generally include a sealing device disposed within a connector (e.g., a patient connector) at the end of catheter tubing, where the sealing device is structurally configured to form a releasable seal for the catheter tubing. That is, when unengaged with a contact portion of another connector or device, the sealing device may be disposed in a first position establishing a seal. Specifically, a channel disposed through the body of the sealing device may be obstructed when in this first position. However, through predetermined engagement with a contact portion of another connector or device, the sealing device may be moved (e.g., rotated) to a second position to establish a fluid pathway through the channel. And, when this predetermined engagement is removed, the sealing device may be structurally configured to automatically move back into the first position to reestablish the seal for the catheter tubing.

In an aspect, a method for releasably sealing a catheter system disclosed herein may include: aligning a first connector and a second connector within a catheter system, the first connector disposed at an end of first tubing and the second connector disposed at an end of second tubing; inserting a contact portion of the second connector within a cavity of the first connector; engaging the contact portion of the second connector with a contact area of a sealing device disposed within the cavity of the first connector, the sealing device disposed in a first position establishing a seal for the first tubing by obstructing a channel disposed through a body of the sealing device; establishing a predetermined engagement of the contact portion of the second connector and the contact area of the sealing device; and rotating the sealing device from the first position to a second position, the second position establishing a fluid pathway through the channel and between the first tubing and the second tubing.

Implementations may include one or more of the following features. The method may further include removing the predetermined engagement of the contact portion of the second connector and the contact area of the sealing device, where removal of the predetermined engagement rotates the sealing device from the second position to the first position thereby reestablishing the seal for the first tubing. The method may further include removing the obstruction of the channel by exposing one or more of a front aperture on a front surface of the sealing device and a rear aperture on a rear surface of the sealing device. The method may further include removing the obstruction of the channel by decompressing the channel during rotation of the sealing device from the first position to the second position. The first connector may be a patient connector attached to a patient, and the second connector may be part of an extension set for the catheter system. The predetermined engagement of the contact portion of the second connector and the contact area of the sealing device may be established by mechanically keying the first connector and the second connector in a predetermined manner. The first connector and the second connector may include Luer lock connectors, where mechanically keying the first connector and the second connector in the predetermined manner includes affixing the second connector to the first connector through relative rotation therebetween.

In an aspect, an apparatus for forming a releasable seal in a catheter system disclosed herein may include a first connector including one or more interior walls defining a cavity that is accessible from an opening on an end of the first connector, and a sealing device disposed within the cavity of the first connector. The sealing device may include a body having a front surface, a rear surface, and a side surface disposed between the front surface and the rear surface that defines a perimeter of the body. The sealing device may further include a channel disposed through the body from a front aperture on the front surface to a rear aperture on the rear surface, a contact area disposed on the front surface of the body and accessible from the opening on the end of the first connector, and a hinge located on the side surface and engaged with an interior wall of the one or more interior walls of the first connector. The hinge may be structurally configured to, upon a predetermined engagement with the contact area, permit rotation of the body within the first connector between a first position and a second position, the first position establishing a seal between the opening of the first connector and at least a portion of the cavity, and the second position establishing a fluid pathway through the channel between the opening of the first connector and at least the portion of the cavity.

Implementations may include one or more of the following features. The hinge may include at least one protrusion from the side surface of the body that is received by a void disposed within the cavity of the first connector. The body of the sealing device may be sized and shaped such that, when the sealing device is in the first position, one or more of the front aperture and the rear aperture is sealed by a wall of the one or more interior walls of the first connector. The body of the sealing device may be deformable such that, when the sealing device is in the first position, the channel is sealed by a wall of the one or more interior walls of the first connector. The wall may deform the body of the sealing device thereby restricting a diameter of the channel to establish the seal. The sealing device may be structurally configured to, upon removal of the predetermined engagement, rotate via the hinge to the first position. A force exerted by a wall of the one or more interior walls of the first connector may establish the rotation of the sealing device to the first position in absence of the predetermined engagement.

In an aspect, a device for forming a releasable seal in a catheter system disclosed herein may include a body having a front surface, a rear surface, and a side surface disposed between the front surface and the rear surface that defines a perimeter of the body, where the body is structurally configured for placement within a first connector of a catheter system. The device may also include a channel disposed through the body from a front aperture on the front surface to a rear aperture on the rear surface, and a contact area disposed on the front surface of the body, where the contact area is structurally configured for engagement with a portion of a second connector of the catheter system that is couplable with the first connector. The device may further include a hinge located on the side surface, the hinge structurally configured to, upon a predetermined engagement of the portion of the second connector and the contact area, permit rotation of the body within the first connector between a first position and a second position, the first position establishing a seal for tubing disposed upstream from the first connector and the second position establishing a fluid pathway through the channel between the second connector and the tubing disposed upstream from the first connector.

Implementations may include one or more of the following features. A channel axis disposed through the channel may intersect a central axis of the device. The channel axis may be disposed at an angle of between about 10-degrees and 40-degrees offset from the central axis. The predetermined engagement between the portion of the second connector and the contact area may include a predetermined force. The predetermined force may be applied at a predetermined angle relative to a plane disposed through the front surface of the body. The predetermined angle may be substantially normal to the plane disposed through the front surface of the body. The predetermined engagement between the portion of the second connector and the contact area may be blocked by a mechanical feature of the first connector, where predetermined rotation of the second connector circumvents blocking by the mechanical feature to establish the predetermined engagement. The channel may be tapered between the front aperture and the rear aperture. The body may be substantially cylindrical. The body may include a silicone material. The body may be wholly formed from the silicone material. The body may be structurally configured to be releasably deformable within the first connector. The body may be structurally configured to be releasably deformable by one or more interior walls of the first connector to permit rotation of the body during the predetermined engagement. The device may further include one or more cutouts disposed on the side surface to facilitate deformation of the body. One or more of the cutouts may be disposed along at least one-third of the perimeter of the body. One or more of the cutouts may be disposed along less than one-half of the perimeter of the body. One or more of the cutouts may be substantially disposed around the entire perimeter of the body. The contact area may include a protrusion extending from the front surface of the body. The contact area may be offset from a central axis disposed through the front surface of the body. The hinge may include at least one protrusion extending from the side surface of the body, where the protrusion is sized and shaped to cooperate with a void disposed within the first connector. The hinge may include at least two opposing protrusions extending from the side surface of the body. The first connector and the second connector may include Luer lock connectors. The second connector may be part of an extension set for the catheter system. The catheter system may be structurally configured for use in a peritoneal dialysis procedure. The portion of the second connector may include one or more of a wall and a rim of the second connector.

In an aspect, a catheter system disclosed herein may include tubing and a first connector disposed at a first end of the tubing, the first connector including one or more interior walls defining a cavity that is accessible from an opening on an end of the first connector. The system may also include a sealing device disposed within the cavity of the first connector. The sealing device may include: a body having a front surface, a rear surface, and a side surface disposed between the front surface and the rear surface that defines a perimeter of the body; a channel disposed through the body from a front aperture on the front surface to a rear aperture on the rear surface; a contact area disposed on the front surface of the body and accessible from the opening on the end of the first connector; and a hinge located on the side surface and engaged with an interior wall of the one or more interior walls of the first connector, the hinge structurally configured to, upon a predetermined engagement with the contact area, permit rotation of the body within the first connector between a first position and a second position, the first position establishing a seal between the opening of the first connector and the tubing, and the second position establishing a fluid pathway through the channel between the opening of the first connector and the tubing.

Implementations may include one or more of the following features. The system may further include a second connector structurally configured for coupling with the first connector, the second connector including a contact portion structurally configured to establish the predetermined engagement with the contact area of the sealing device when the first connector and the second connector are coupled. Decoupling of the second connector from the first connector may remove the predetermined engagement. Removing the predetermined engagement may cause rotation of the sealing device to the first position thereby establishing the seal. The second connector may be coupled to second tubing. The second connector and the second tubing may be part of a catheter extension set. The contact portion may include one or more of a wall and a rim of the second connector. The contact portion may include a protrusion of the second connector. One or more of the first connector and the second connector may be structurally configured such that the predetermined engagement cannot be established unless a predetermined coupling is established between the first connector and the second connector. The predetermined coupling may include a predetermined rotation between the first connector and the second connector. A second end of the tubing may be connected to a catheter.

These and other features, aspects, and advantages of the present teachings will become better understood with reference to the following description, examples, and appended claims.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "front," "rear," "top," "bottom," "up," "down," and the like, are words of convenience and are not to be construed as limiting terms unless specifically stated to the contrary.

In general, the devices, systems, kits, and methods disclosed herein may generally relate to releasably sealing a connector (or another end, junction, or region) of catheter tubing or portion of a catheter system generally. For example, a connector, and more specifically a sealing device disposed within the connector, may be configured to permit fluid flow therethrough when the connector is engaged with another connector in a predetermined (e.g., mechanically keyed) manner, and, when such engagement is released (e.g., through removal of the other connector), the sealing device may automatically close to block fluid flow therethrough, e.g., through movement of the sealing device or a portion thereof. In this manner, a user may not need to perform any actions beyond removing a connector to seal a portion of a catheter system, nor would a catheter system need a separate sealing component such as a pin, cap, or clamp. This may represent a vast improvement over existing techniques that involve, e.g., the insertion of a cap or pin that can be dislodged or misplaced.

Thus, the present teachings may include a sealing device within a connector (e.g., a patient connector, which will be understood to include a connector along a portion of catheter tubing that is connected, directly or indirectly, to a user such as a dialysis patient or the like) that, when unengaged with a contact portion of another connector or device, establishes a seal. To this end, a channel disposed through the body of the sealing device may be obstructed when in a sealed position. To release this seal, predetermined engagement with a contact portion of another connector or device may move the sealing device (e.g., rotate the sealing device) to establish a fluid pathway through the channel. And, when this predetermined engagement is removed, the sealing device may be structurally configured to automatically move back into the first position to reestablish the seal for the catheter tubing.

It will be understood that aspects of the present teachings may be used to seal catheter tubing and/or other medical tubing and the like. Moreover, although the present disclosure may emphasize the use of the present teachings for releasably sealing a patient connector of catheter tubing, other portions and/or connectors of a catheter system, catheter tubing, and/or catheter apparatus, may utilize one or more aspects of the present teachings. An advantageous use case for aspects of the present teachings may be within a connector disposed at the end of catheter tubing protruding from a patient's body (which, again, is generally referred to herein as a patient connector) for procedures such as peritoneal dialysis, e.g., when the patient is a kidney patient. However, it will be understood that other use cases are possible, including without limitation, for releasably sealing catheter tubing used for administering medicines, establishing drainage, taking biological samples, for surgical procedures, and the like. In an aspect, the present teachings include a catheter extension apparatus where one or more connectors thereon includes a releasable sealing device as disclosed herein.

Therefore, in an aspect, and as explained herein, the present teachings may include a self-closing silicone plug for catheter applications. That is, a sealing device disclosed herein may include a silicone-based self-occluding design for catheter extension sets with patient connector applications. That is, the sealing device—e.g., through its specific geometric features—may have the property of a self-occluding valve mechanism for peritoneal dialysis applications. In an aspect, when a connector is inserted into a patient connector containing a sealing device as described herein, a portion of the inserted connector may create a displacement for the sealing device in the patient connector. This displacement may align the fluid path within the patient connector to allow fluid to flow, e.g., allowing a treatment to begin/continue. Once a treatment is finished, and the connector is removed from the patient connector, the specific geometry of the patient connector and sealing device may work together to realign the sealing device back to its original, sealed position within the patient connector. This may occlude the catheter tubing without a need for external mechanisms. As discussed herein, it will be understood that a sealing device according to the present teachings may also or instead be included within a connector (or another portion of catheter tubing) that is connected to a patient connector, and where the patient connector may not necessarily include such a sealing device.

Figure 1:
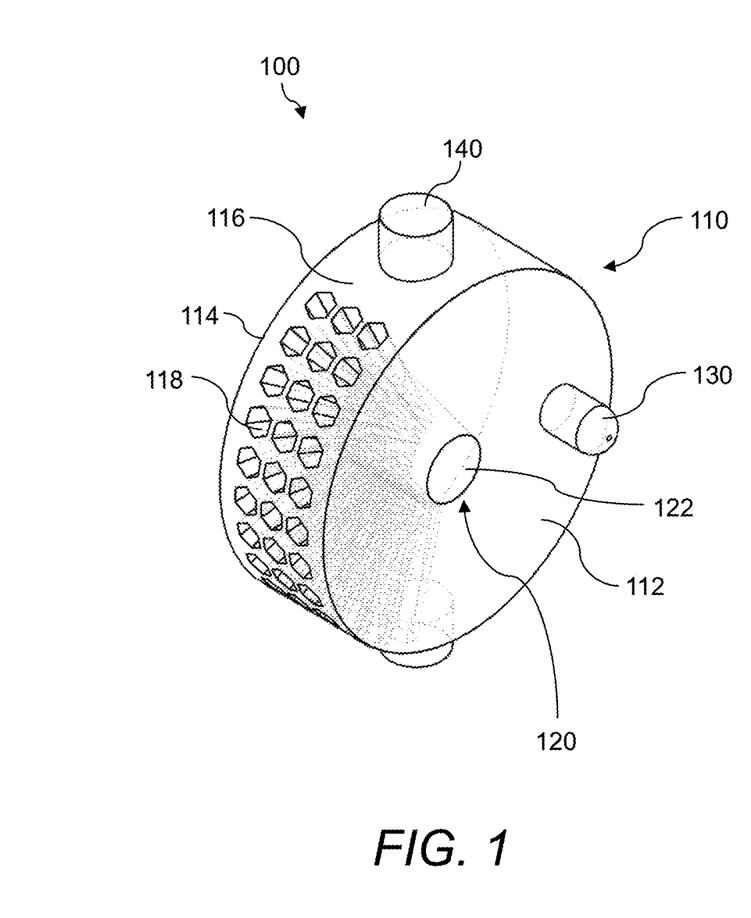
FIG. 1 illustrates a sealing device, in accordance with a representative embodiment.
Figure 2:
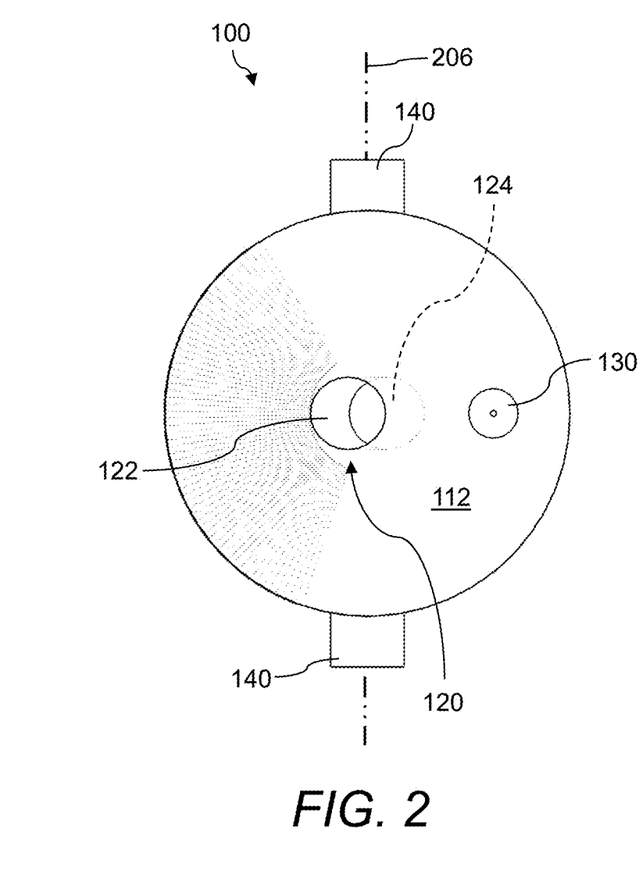
FIG. 2 illustrates a front view of a sealing device, in accordance with a representative embodiment.
Figure 3:
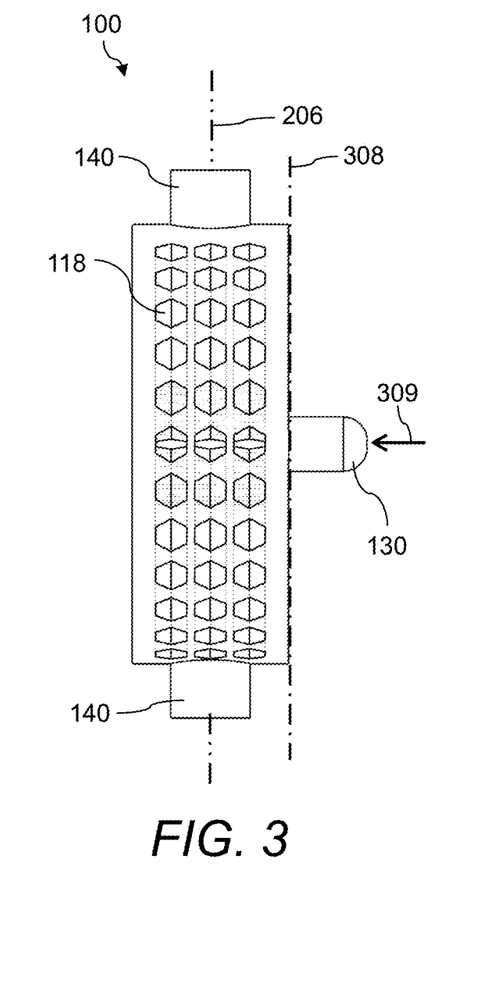
FIG. 3 illustrates a side view of a sealing device, in accordance with a representative embodiment.
Figure 4:
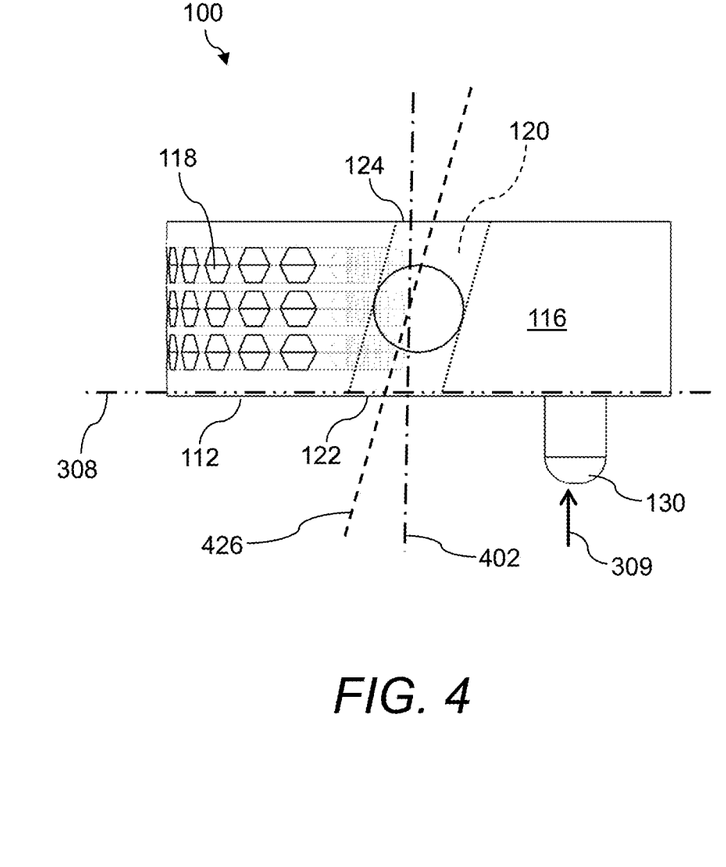
FIG. 4 illustrates a top view of a sealing device, in accordance with a representative embodiment.

FIG. 1 illustrates a sealing device, FIG. 2 illustrates a front view of a sealing device, FIG. 3 illustrates a side view of a sealing device, and FIG. 4 illustrates a top view of a sealing device, in accordance with a representative embodiment. Thus, it will be understood that the device 100 shown in FIGS. 1-4 may be the same device 100, but shown from different views for understanding of its various features and advantages. The device 100 may generally be a component that is structurally configured to form a releasable seal in a catheter system, or otherwise in catheter tubing. Thus, it shall be understood that although the device 100 may be described as being present within a connector such as a patient connector, or more particularly as being disposed within a "first connector," the device 100 may also or instead be disposed in another portion of a catheter system or apparatus. The device 100 may generally include a body 110 (e.g., a singular body that defines the entire shape and configuration of the device 100), a channel 120 disposed through the body 110, a contact area 130 for engagement with another component to move the device 100 when disposed within a portion of a catheter system such as a connector, and a hinge 140 or the like to facilitate such movement.

The body 110 of the device 100 may be structurally configured for placement within a first connector of a catheter system, e.g., a patient connector as defined herein, or another connector such as that on a catheter extension apparatus. In an aspect, the body 110 may have a front surface 112, a rear surface 114, and a side surface 116 disposed at least partially between the front surface 112 and the rear surface 114. For example, the side surface 116 may define a perimeter of the body 110. In this manner, the body 110 may be substantially cylindrical and/or disc-shaped as shown in the figures, although other shapes are possible as will be understood by a skilled artisan. For example, although shown as having a substantially circular profile, the body 110 may have a profile that is defined by a different shape, such as being substantially oval or otherwise shaped. Further, it will be understood that, although the front surface 112 and the rear surface 114 are shown as being substantially the same size and shape, other configurations are possible where the front surface 112 and the rear surface 114 do not have the same size and/or shape.

The body 110 of the device 100 may include a silicone material or similar. For example, in an aspect, the body 110 is wholly formed from such a silicone material or similar. In general, the body 110 of the device 100 may be made of a substantially flexible material so that the body 110 can be releasably deformable within a portion of a catheter system such as a connector. Being releasably deformable within a portion of a catheter system may be advantageous for movement of the device 100 within the catheter system and/or for reconfiguring the channel 120 disposed therethrough (e.g., where the body 110 is compressible to constrict or close the channel 120 by restricting a diameter thereof, and expandable to open the channel 120 by increasing a diameter thereof). By way of example, when the device 100 is included in a first connector, the body 110 may be structurally configured to be releasably deformable within the first connector. More specifically, the body 110 may be structurally configured to be releasably deformable by one or more interior walls of the first connector to permit movement (e.g., rotation) of the body 110 during a predetermined engagement as described herein.

The channel 120 of the device 100 may be disposed through the body 110 from a front aperture 122 on the front surface 112 to a rear aperture 124 on the rear surface 114. It is also or instead possible that the channel 120 includes an aperture on the side surface 116 of the device 100. In general, the channel 120 may define a fluid pathway through the device 100 that is closed (e.g., obstructed) when the device 100 is in a first position within a first connector, and that is open (e.g., unobstructed) when the device 100 is in a second position within the first connector. Thus, the first position as described herein may be a sealed position, and the second position as described herein may be an open, non-sealed position within a connector or another portion of a catheter system or apparatus.

As best shown in FIG. 2 and FIG. 4, the channel 120 may be offset within the body 110 of the device 100. That is, the channel 120 may be disposed at an angle relative to a plane 308 defined by one or more of the front surface 112 and the rear surface 114 of the device 100. That is, the front aperture 122 on the front surface 112 may not be aligned with the rear aperture 124 on the rear surface 114, but rather these apertures may be offset relative to one another on their respective surfaces of the body 110 of the device 100. Stated otherwise, and as shown in FIG. 4, a channel axis 426 disposed through the channel 120 may intersect a central axis 402 of the device 100. For example, the channel axis 426 may be disposed at an angle of between about 10-degrees and about 40-degrees offset from the central axis 402 (e.g., about 25-degrees). The angle and general disposition of the channel 120 through the body 110 may be selected and structurally configured to provide for a blocking of a fluid pathway through the channel 120 when the device 100 is in the first position as described herein—e.g., through positioning of the device 100 such that a portion of a connector in which the device 100 is disposed (e.g., an interior wall of the first connector as described herein) blocks an aperture of the channel 120, and/or through a deformation of the device 100 such that the channel 120 is constricted to a point of occluding a fluid pathway through the channel 120 when the device 100 is in the first position.

In certain aspects, the channel 120 may be tapered between the front aperture 122 and the rear aperture 124. For example, in an aspect, the channel 120 may be structurally configured to be constricted toward the rear aperture 124 when in the first position. To this end, the channel 120 may be advantageously tapered with a decreasing inner diameter from the front aperture 122 to the rear aperture 124 such that the deformation need not be as dramatic to seal the channel 120. The channel 120 may also or instead be tapered for other reasons including without limitation for promoting certain fluid flows through the body 110 of the device 100 when in use. In certain aspects, the channel 120, and more specifically an aperture thereof, may be structurally configured to receive a portion of a connector or another component—e.g., a needle or other conduit for directing fluid within the channel 120.

The contact area 130 of the device 100 may be disposed on the front surface 112 of the body 110. It will be understood, however, that the contact area 130 of the device 100 may also or instead be disposed on another portion of the device 100, such as the rear surface 114 of the body 110 and/or the side surface 116 of the body 110. In general, the contact area 130 may be structurally configured for engagement with a portion of a second connector or another component of a catheter system, e.g., a second connector of the catheter system that is couplable with a first connector that contains the device 100. As shown in the figures, the contact area 130 may include a protrusion extending from a surface (e.g., the front surface 112) of the body 110. However, it will be understood that the contact area 130 need not be defined by such a protrusion—e.g., the contact area 130 may merely comprise a region of the front surface 112 of the body 110 with no discernable features, the contact area 130 may include an indent or void on the front surface 112 of the body 110, and so on. The contact area 130 may be offset from one or more of a rotation axis 206 (see, e.g., FIGS. 2 and 3) disposed vertically through the device 100, and a central axis 402 disposed through the front surface 112 of the body 110 as shown in FIG. 4. The contact area 130 being offset from one or more of these axes may be advantageous in embodiments where the device 100 is configured to rotate within a structure of a catheter system such as a connector. That is, when a predetermined force is provided at an offset location from these axes, this force may cause the device 100 to rotate about the rotation axis 206.

Predetermined engagement with the contact area 130 may involve application of a predetermined force. For example, predetermined engagement between a portion of a second connector (being coupled to the first connector that includes the device 100) and the contact area 130 may include a predetermined force. This predetermined force may be applied at a predetermined angle relative to a plane 308 (see, e.g., FIGS. 3 and 4) disposed through the front surface 112 of the body 110. The predetermined angle may be substantially normal to the plane 308 disposed through the front surface 112 of the body 110 as shown by the arrow 309 of FIGS. 3 and 4. Other angles for this force are also or instead possible.

Movement (e.g., rotation) of the device 100 within a structure of a catheter system such as a first connector may be facilitated via a hinge 140 or the like. The hinge 140 may be located on the side surface 116 of the body 110 of the device 100, although it will be understood that the hinge 140 may also or instead be located or attached to other surfaces such as the front surface 112 and/or the rear surface 114. When the device 100 is disposed within a first connector that is structurally configured to engage with a second connector in a catheter system or the like, the hinge 140 may be structurally configured to, upon a predetermined engagement of a portion of the second connector and the contact area 130, permit rotation of the body 110 within the first connector between a first position and a second position. As described herein, the first position may establish a seal for tubing disposed upstream from the first connector and the second position may establish a fluid pathway through the channel 120 between the second connector and the tubing disposed upstream from the first connector.

As shown in the figures, the hinge 140 may include at least one protrusion extending from the side surface 116 of the body 110. In this manner, the hinge 140 may be sized and shaped to cooperate with a void disposed within the first connector or another structure to which the device 100 is engaged. In certain aspects, and as shown in the figures, the hinge 140 may include at least two opposing protrusions extending from the side surface 116 of the body 110. The hinge 140 may also or instead include a pin or the like that is disposed through the body 110 of the device 100.

In lieu of, or in addition to such a hinge 140, other mechanical structures may be provided on the device 100 to facilitate its movement within a structure of a catheter system such as a first connector, e.g., between the first position (e.g., a sealed position) and the second position (e.g., an open, non-sealed position). For example, the device 100 may also or instead include a pivot point, a bearing, a slider, a toggle, and the like.

The device 100 may further include one or more cutouts 118 disposed on the side surface 116 of the body 110. These cutouts 118 may work to facilitate deformation of the body 110, e.g., by adding flexibility to the body 110. The cutouts 118 may be wholly or partially disposed around a perimeter of the body 110. For example, the cutouts 118 may be disposed along at least one-third of the perimeter of the body 110; the cutouts 118 may be disposed along less than one-half of the perimeter of the body 110; or the cutouts 118 may be substantially disposed around the entire perimeter of the body 110. Other configurations are also or instead possible.

Figure 5:
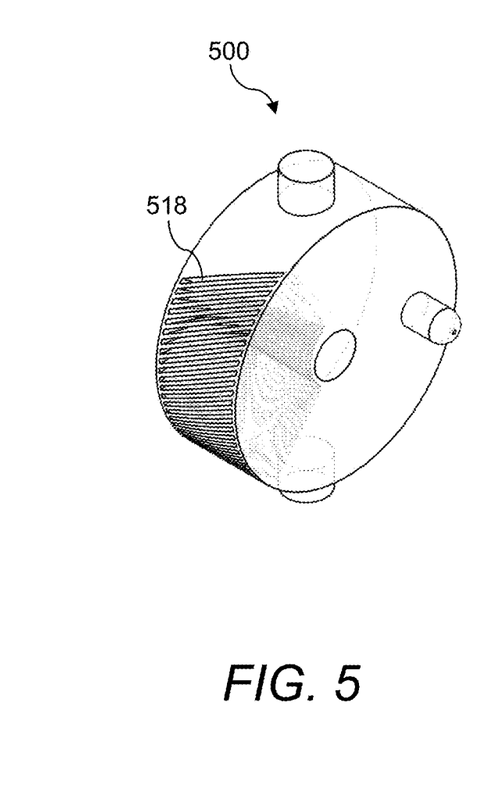
FIG. 5 illustrates a sealing device, in accordance with a representative embodiment.
Figure 6:
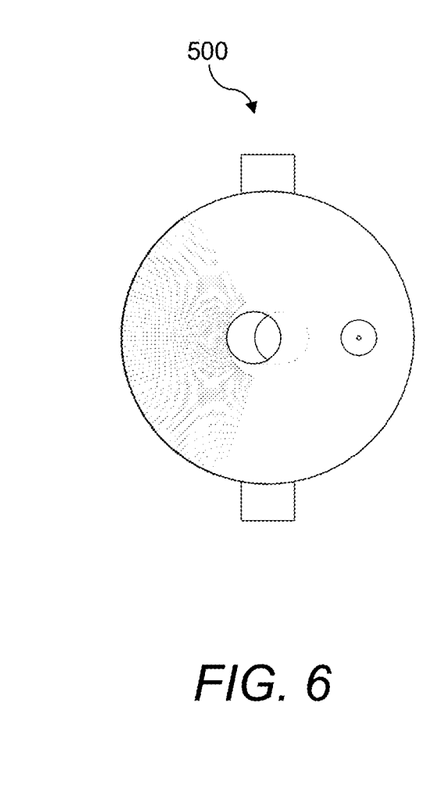
FIG. 6 illustrates a front view of a sealing device, in accordance with a representative embodiment.
Figure 7:
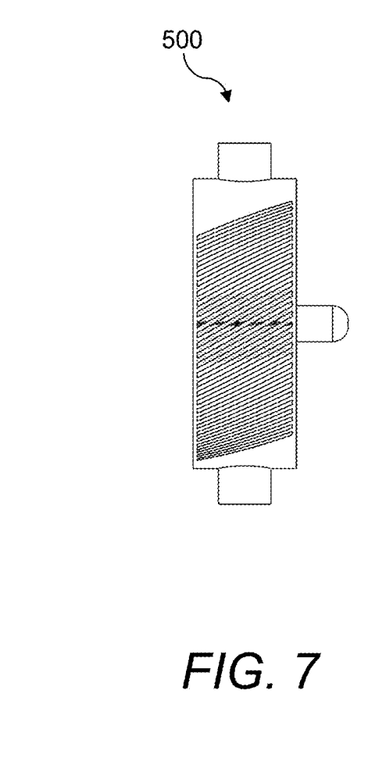
FIG. 7 illustrates a side view of a sealing device, in accordance with a representative embodiment.

FIG. 5 illustrates a sealing device, FIG. 6 illustrates a front view of a sealing device, and FIG. 7 illustrates a side view of a sealing device, in accordance with a representative embodiment. The device 500 shown in each of FIGS. 5-7 may be the same device 500. Further, the device 500 shown in FIGS. 5-7 may be the same or similar to the device 100 shown and described above, but where the cutouts 518 are shown as slits in FIGS. 5-7 instead of polygons as in FIGS. 1-4. It will be understood that other shapes for the cutouts 518 are also or instead possible, including without limitation other polygons, curves shapes (e.g., circles, ovals, ellipses, and so on), fanciful shapes (e.g., stars, hearts, corporate logos, lettering, numbering, symbols, and so on), and the like. Further, it will be understood that the number of cutouts 518 may vary without departing from the scope of this disclosure, including embodiments devoid of any such cutouts 518.

Figure 8:
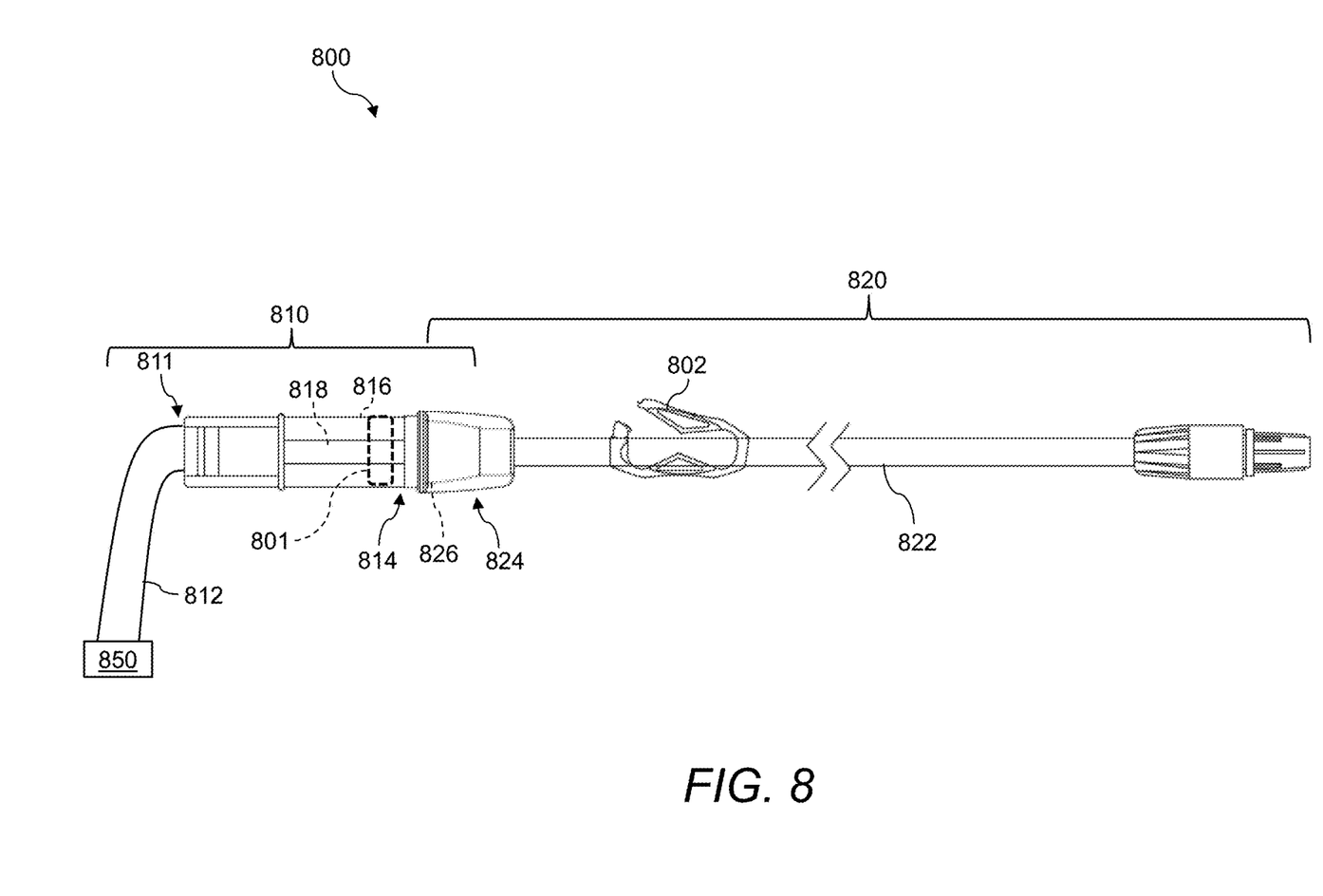
FIG. 8 illustrates a catheter system, in accordance with a representative embodiment.

FIG. 8 illustrates a catheter system, in accordance with a representative embodiment. The system 800 may generally include a first apparatus 810 and a second apparatus 820, where each of these apparatuses include one or more connectors structurally configured for engagement with a cooperating connector of another apparatus. One or more of the first apparatus 810 and the second apparatus 820 may further include tubing—e.g., the first apparatus 810 may include first tubing 812 and the second apparatus 820 may include second tubing 822. One or more of the first apparatus 810 and the second apparatus 820 may include a portion of the system 800 that is connected to a patient, or that is structurally configured for connection to a patient. Further, one or more of the first apparatus 810 and the second apparatus 820 may include a part of a catheter extension set. By way of example, the first apparatus 810 may include a first connector 814 in the form of a patient connector, and the second apparatus 820 may include at least a part of a catheter extension set, where the second apparatus 820 includes a second connector 824 structurally configured for engagement with the first connector 814.

One or more of the first apparatus 810 and the second apparatus 820 may be structurally configured for forming a releasable seal in the system 800 as described herein. For example, the first apparatus 810 may include a first connector 814 disposed at a first end 811 of the first tubing 812. The first connector 814 may include one or more interior walls 816 defining a cavity 818 that is accessible from an opening on an end of the first connector 814. The first apparatus 810 may further include a sealing device 801 disposed within the cavity 818 of the first connector 814.

The sealing device 801 may be the same or similar to any as described herein, e.g., with reference to any of FIGS. 1-7 described above. For example, the sealing device 801 may include a body having a front surface, a rear surface, and a side surface disposed between the front surface and the rear surface that defines a perimeter of the body. The sealing device 801 may further include a channel disposed through the body from a front aperture on the front surface to a rear aperture on the rear surface, a contact area disposed on the front surface of the body and accessible from the opening on the end of the first connector 814, and a hinge located on the side surface and engaged with an interior wall 816 of the first connector 814. The hinge of the sealing device 801 may be structurally configured to, upon a predetermined engagement with the contact area, permit rotation of the body of the sealing device 801 within the first connector 814 between a first position and a second position. As described herein, the first position may establish a seal between the opening of the first connector 814 and at least a portion of the cavity 818 (and/or between the opening of the first connector 814 and the first tubing 812), and the second position may establish a fluid pathway through the channel of the sealing device 801 between the opening of the first connector 814 and at least the portion of the cavity 818 (and/or between the opening of the first connector 814 and the first tubing 812).

As discussed above, the second apparatus 820 may include a second connector 824 structurally configured for coupling with the first connector 814. The second connector 824 may further be structurally configured to engage with the sealing device 801, e.g., for moving the sealing device 801 between the first position and the second position. For example, the sealing device 801 may be structurally configured to be in the first position (a sealed position) when the first connector 814 is uncoupled from another connector, e.g., the second connector 824. However, upon a predetermined engagement, which may be provided through a coupling of the first connector 814 with the second connector 824, the sealing device 801 may be structurally configured to move into and maintain the second position (an unsealed position). Maintaining the second position may thus be provided by a force being applied (e.g., a constant) force by a portion of the second connector 824 or another component. Maintaining the second position may also or instead be provided by, or reinforced by, one or more of a flow of fluid through the connectors, an interior wall 816 of the first connector 814, and the like.

Decoupling of the second connector 824 from the first connector 814 may remove this predetermined engagement, thereby returning the sealing device 801 to the first position (a sealed position) automatically upon such a decoupling. For example, removing the predetermined engagement may cause rotation of the sealing device 801 to the first position thereby establishing a seal for the first apparatus 810.

In this manner, the second connector 824 may include a contact portion 826 structurally configured to establish the predetermined engagement with the contact area of the sealing device 801 when the first connector 814 and the second connector 824 are coupled, e.g., in a predetermined arrangement. To this end, in certain aspects, the predetermined engagement may involve the second connector 824 being mechanically keyed to the first connector 814. By way of example, in certain implementations, the first connector 814 and the second connector 824 include Luer lock connectors or the like. Further, a proper configuration, alignment, and/or movement of the second connector 824 and the first connector 814 relative to one another may be needed to couple the connectors and/or establish the predetermined engagement. Stated otherwise, one or more of the first connector 814 and the second connector 824 may be structurally configured such that the predetermined engagement cannot be established unless a predetermined coupling is established between the first connector 814 and the second connector 824. By way of example, in certain aspects, the predetermined engagement between at least a portion of the second connector 824 and the contact area of the sealing device 801 may be blocked by a mechanical feature of the first connector 814. And in such instances, a predetermined rotation (or other movement) of the second connector 824 relative to the first connector 814 (or vice-versa) may circumvent this blocking by the mechanical feature to establish the predetermined engagement. Thus, the predetermined coupling may include a predetermined rotation between the first connector 814 and the second connector 824. This mechanical feature may be a wall, a protrusion, a screw thread (or other thread), a channel wall, and the like.

The portion of the second connector 824 that engages the contact area of the sealing device 801 for moving the sealing device 801 from the first position to the second position may include one or more of a wall of the second connector 824, a rim (e.g., a leading edge) of the second connector 824, a protrusion of the second connector 824, and the like. The portion of the second connector 824 that engages the contact area of the sealing device 801 for moving the sealing device 801 from the first position to the second position may be disposed on the interior of the second connector 824, the exterior of the second connector 824, or both.

Movement of the sealing device 801 within and relative to the first connector 814 may be facilitated by a hinge, which may include any of the hinges or similar structures described herein. For example, the hinge may include at least one protrusion from the side surface of the body of the sealing device 801 that is received by a void (e.g., a cutout or the like) disposed within the cavity 818 of the first connector 814. Thus, the sealing device 801 may be structurally configured to, upon establishment of the predetermined engagement, rotate via the hinge to the second position; and the sealing device 801 may be structurally configured to, upon removal of the predetermined engagement, rotate via the hinge to the first position. Further, the sealing device 801 may form a seal in the first position in the same or similar manner as described above. For example, the body of the sealing device 801 may be sized and shaped such that, when the sealing device 801 is in the first position, one or more of its front aperture and its rear aperture of the channel may be sealed by an interior wall 816 of the first connector 814. Also or instead, the body of the sealing device 801 may be deformable such that, when the sealing device 801 is in the first position, the channel is sealed by an interior wall 816 of the first connector 814. To this end, an interior wall 816 may deform the body of the sealing device 801 thereby restricting a diameter of the channel to establish a seal in the first position. An interior wall 816 may also or instead facilitate or otherwise assist in movement of the sealing device 801 between the first position and the second position. For example, a force exerted by an interior wall 816 of the first connector 814 may establish the rotation of the sealing device 801 to the first position in absence of the predetermined engagement—e.g., by squeezing or otherwise providing a force or pressure on the sealing device 801 thereby promoting its movement.

It will be understood that one or more of the first connector 814 and the second connector 824 in the system 800 may be the same or similar to any of the connectors described elsewhere herein. For example, as described herein, the catheter system 800 may be structurally configured for use in a peritoneal dialysis procedure. Thus, one or more of the first connector 814 and the second connector 824 may be specifically designed for use in a dialysis procedure. One or more of the first connector 814 and the second connector 824 may also or instead be part of a generic catheter tubing kit, set, or component. By way of example, the second connector 824 may be part of an extension set for the system 800. In this manner, and as shown in the figure, the second connector 824 may be coupled to second tubing 822. Further, one or more ends of the tubing (e.g., the first tubing 812 or the second tubing 822) may be connected to a catheter 850, which is shown by way of representation.

The system 800 may thus be structurally configured to allow a user (e.g., a patient with a catheter temporarily or permanently connected to their body) to have a secured, leak-free connector that is self-sealing. It will thus be understood that the sealing device 801 included in the system 800 may alleviate any need for the clamp 802 that is optionally shown. In this manner, the system 800 may merely include a clamp 802 for redundancy.

Figure 9:
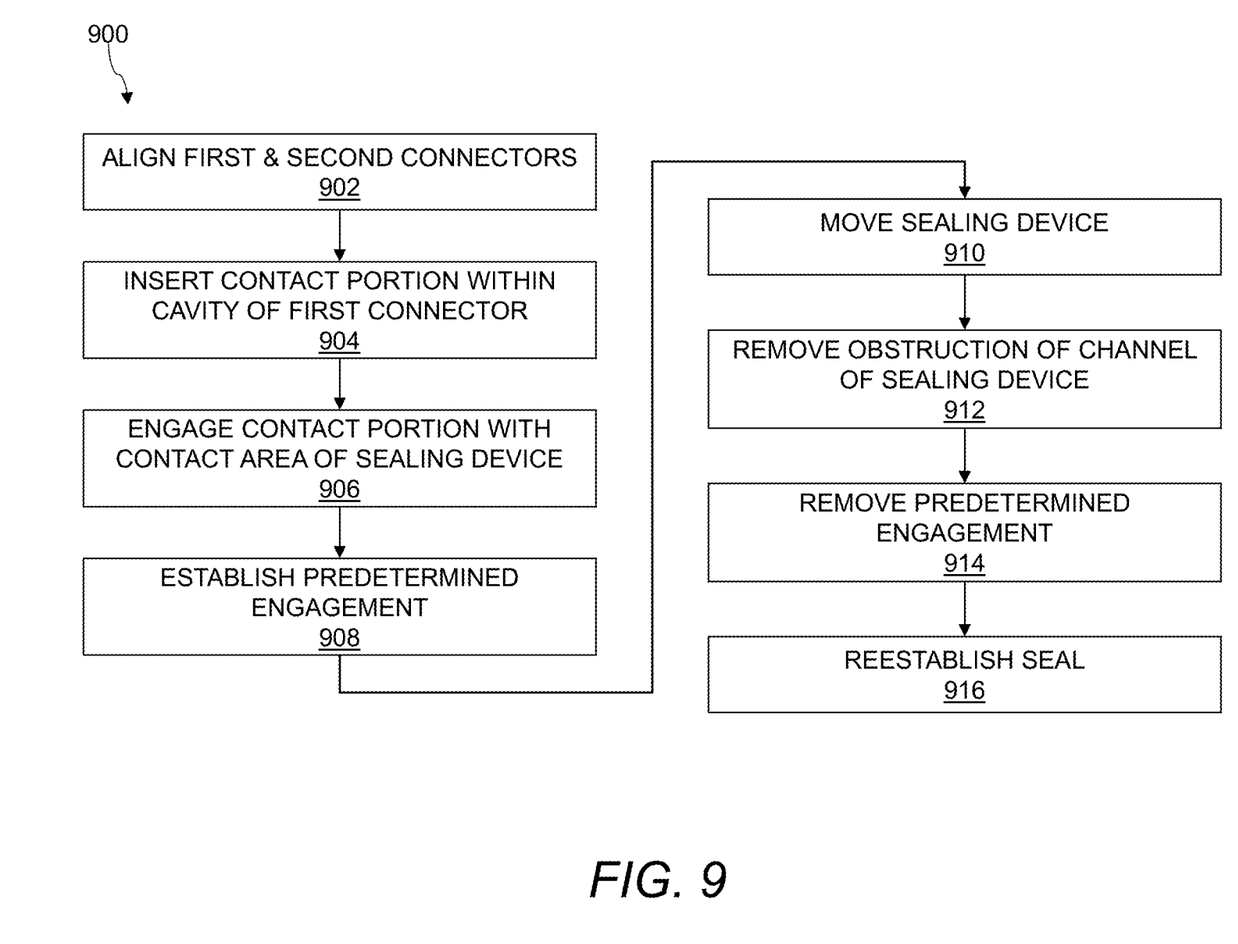
FIG. 9 is a flow chart of a method for releasably sealing a catheter system, in accordance with a representative embodiment.

FIG. 9 is a flow chart of a method for releasably sealing a catheter system, in accordance with a representative embodiment. The method 900 may be performed using any of the devices, systems, apparatuses, and kits described herein. Thus, any of the components recited in the method 900 will be understood as potentially including any of the corresponding components described herein, e.g., with reference to the other figures.

As shown in step 902, the method 900 may include aligning a first connector and a second connector within a catheter system. The first connector may be disposed at an end of first tubing and the second connector may be disposed at an end of second tubing. As described herein, in some implementations, the first connector is a patient connector attached to a patient, and the second connector is part of an extension set for a catheter system.

As shown in step 904, the method 900 may include inserting a contact portion of the second connector within a cavity of the first connector. This insertion may occur during engagement or coupling of the first connector and the second connector. For example, by performing a somewhat standard engagement between the first connector and the second connector (e.g., by pushing the second connector onto or within the first connector (or vice-versa), by screwing the second connector onto or into the first connector (or vice-versa), and the like), the contact portion of the second connector may be configured to enter the cavity of the first connector.

As shown in step 906, the method 900 may include engaging the contact portion of the second connector with a contact area of a sealing device disposed within the cavity of the first connector. Before such engagement, the sealing device may be disposed in a first position establishing a seal for the first tubing by obstructing a channel disposed through a body of the sealing device. Thus, the sealing device may be the same or similar to those described elsewhere herein.

As shown in step 908, the method 900 may include establishing a predetermined engagement of the contact portion of the second connector and the contact area of the sealing device. As described herein, the predetermined engagement of the contact portion of the second connector and the contact area of the sealing device may be established by mechanically keying the first connector and the second connector in a predetermined manner. For example, the first connector and the second connector may include Luer lock connectors, where mechanically keying the first connector and the second connector in the predetermined manner includes affixing the second connector to the first connector through relative motion and/or force (e.g., rotation) therebetween.

As shown in step 910, the method 900 may include moving the sealing device. For example, this step 910 may include rotating the sealing device from the first position to a second position. As described herein, the second position may establish a fluid pathway through the channel and between the first tubing and the second tubing.

In this manner, as shown in step 912, the method 900 may include removing an obstruction of the channel of the sealing device. Removing the obstruction may occur by exposing one or more of a front aperture on a front surface of the sealing device and a rear aperture on a rear surface of the sealing device. Removing the obstruction may also or instead occur by decompressing the channel during rotation or other movement of the sealing device from the first position to the second position.

As shown in step 914, the method 900 may include removing the predetermined engagement of the contact portion of the second connector and the contact area of the sealing device. As discussed herein, removal of the predetermined engagement may rotate or otherwise move the sealing device from the second position to the first position thereby reestablishing the seal for the first tubing. Thus, in this manner, as shown in step 916, the method 900 may include reestablishing the seal.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. An apparatus for forming a releasable seal in a catheter system, the apparatus comprising:
   a first connector including one or more interior walls defining a cavity that is accessible from an opening on an end of the first connector; and
   a sealing device disposed within the cavity of the first connector, the sealing device comprising:
   a body having a front surface, a rear surface, and a side surface disposed between the front surface and the rear surface that defines a perimeter of the body;
   a channel disposed through the body from a front aperture on the front surface to a rear aperture on the rear surface;
   a contact area disposed on the front surface of the body and accessible from the opening on the end of the first connector; and
   a hinge located on the side surface and engaged with an interior wall of the one or more interior walls of the first connector, the hinge structurally configured to, upon a predetermined engagement with the contact area, permit rotation of the body within the first connector between a first position and a second position, the first position establishing the seal between the opening of the first connector and at least a portion of the cavity, and the second position establishing a fluid pathway through the channel between the opening of the first connector and at least the portion of the cavity, wherein the body of the sealing device is deformable such that, when the sealing device is in the first position, the channel is sealed by a wall of the one or more interior walls of the first connector.

2. The apparatus of claim 1, wherein the hinge includes at least one protrusion protruding from the side surface of the body that is received by a void disposed within the cavity of the first connector.

3. The apparatus of claim 1, wherein the body of the sealing device is sized and shaped such that, when the sealing device is in the first position, one or more of the front aperture and the rear aperture is sealed by a wall of the one or more interior walls of the first connector.

4. The apparatus of claim 1, wherein the wall is configured to deform the body of the sealing device thereby restricting a diameter of the channel to establish the seal.

5. The apparatus of claim 1, wherein the sealing device is structurally configured to, upon removal of the predetermined engagement, rotate via the hinge to the first position.

6. The apparatus of claim 5, wherein a force exerted by a wall of the one or more interior walls of the first connector establishes the rotation of the sealing device to the first position in absence of the predetermined engagement.

7. A catheter system, comprising:
   a tubing;
   a first connector disposed at a first end of the tubing, the first connector including one or more interior walls defining a cavity that is accessible from an opening on an end of the first connector;
   a sealing device disposed within the cavity of the first connector, the sealing device comprising:
   a body having a front surface, a rear surface, and a side surface disposed between the front surface and the rear surface that defines a perimeter of the body;
   a channel disposed through the body from a front aperture on the front surface to a rear aperture on the rear surface;
   a contact area disposed on the front surface of the body and accessible from the opening on the end of the first connector; and
   a hinge located on the side surface and engaged with an interior wall of the one or more interior walls of the first connector, the hinge structurally configured to, upon a predetermined engagement with the contact area, permit rotation of the body within the first connector between a first position and a second position, the first position establishing a seal between the opening of the first connector and the tubing, and the second position establishing a fluid pathway through the channel between the opening of the first connector and the tubing; and a second connector structurally configured for coupling with the first connector, the second connector including a contact portion structurally configured to establish the predetermined engagement with the contact area of the sealing device when the first connector and the second connector are coupled, wherein decoupling of the second connector from the first connector removes the predetermined engagement, and wherein removing the predetermined engagement causes rotation of the sealing device to the first position thereby establishing the seal.

8. The system of claim 7, wherein one or more of the first connector and the second connector are structurally configured such that the predetermined engagement cannot be established unless a predetermined coupling is established between the first connector and the second connector.

9. The system of claim 8, wherein the predetermined coupling includes a predetermined rotation between the first connector and the second connector.

10. The system of claim 7, wherein the first connector is a patient connector attached to a patient, and wherein the second connector is part of an extension set for the catheter system.

11. The system of claim 7, wherein the contact portion includes one or more of a wall of the second connector, a rim of the second connector, and a protrusion of the second connector.

12. A device for forming a releasable seal in a catheter system, the device comprising:

a body having a front surface, a rear surface, and a side surface disposed between the front surface and the rear surface that defines a perimeter of the body, wherein the body is structurally configured for placement within a first connector of the catheter system;

a channel disposed through the body from a front aperture on the front surface to a rear aperture on the rear surface;

a contact area disposed on the front surface of the body, the contact area structurally configured for engagement with a portion of a second connector of the catheter system that is couplable with the first connector; and a hinge located on the side surface, the hinge structurally configured to, upon a predetermined engagement of the portion of the second connector and the contact area, permit rotation of the body within the first connector between a first position and a second position, the first position establishing the seal for a tubing disposed upstream from the first connector and the second position establishing a fluid pathway through the channel between the second connector and the tubing disposed upstream from the first connector, wherein the body is deformable such that, when the body is in the first position, the channel is sealed by a wall of the first connector.

13. The device of claim 12, wherein a channel axis disposed through the channel intersects a central axis of the device.

14. The device of claim 12, wherein the predetermined engagement between the portion of the second connector and the contact area includes a predetermined force.

15. The device of claim 12, wherein the channel is tapered between the front aperture and the rear aperture.

16. The device of claim 12, wherein the contact area is offset from a central axis disposed through the front surface of the body.

17. The device of claim 12, wherein the wall of the first connector is configured to deform the body when in the first position thereby restricting a diameter of the channel to establish the seal.

18. The device of claim 12, wherein the body is structurally configured to, upon removal of the predetermined engagement, rotate via the hinge to the first position.

19. The device of claim 18, wherein a force exerted by the wall of the first connector establishes the rotation of the body to the first position in absence of the predetermined engagement.

20. The device of claim 12, wherein the body includes a silicone material.

* * * * *